US00PP34727P2

(12) United States Plant Patent
Blom

(10) Patent No.: US PP34,727 P2
(45) Date of Patent: Nov. 8, 2022

(54) ***HOSTA* PLANT NAMED 'VER10234'**

(50) Latin Name: *Hosta undulata*
Varietal Denomination: VER10234

(71) Applicant: Arie Blom, Vleuten (NL)

(72) Inventor: Arie Blom, Vleuten (NL)

(73) Assignee: HEEMSKERK VASTEPLANTEN BV, Noordwijk (NL)

( * ) Notice: Subject to any disclaimer, the term of this patent is extended or adjusted under 35 U.S.C. 154(b) by 0 days.

(21) Appl. No.: 17/468,380

(22) Filed: Sep. 7, 2021

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12
See application file for complete search history.

(56) References Cited

PUBLICATIONS

Southern Living, "White Feather *Hosta* is the Unexpected Accent Your Shade Garden Needs", Jun. 26, 2019, downloaded fromhttps://www.yahoo.com/now/white-feather-hosta-unexpected-accent-180639645.html?guccounter=1&guce_referrer=aHR0cHM6Ly93d3cuZ29vZ2xlLmNvbS8&guce_referrer_sig=AQAAAN54j7alM5U0nFq2iJCMkntdl8Vj40OGmD4.*

Mickfield *Hostas* Newsletter, Tetraploid cultivars, Issue 45, Sep. 2010, downloaded from https://www.mickfieldhostas.co.uk/newsletters/September_2010.pdf.*

Zolock, Polyploidy in Daylily and *Hosta*, Aug. 16, 2003, downloaded from http://www.hostalibrary.org/misc/hybrid/polyploidy.pdf.*

Hort.Net, *Hosta* tetraploidy inducements using surflan by Tony Avent, Feb. 26, 2001, downloaded from https://www.hort.net/lists/hosta-open/feb01/msg00561.html.*

Zonneveld and Pollock, Plant Biology, Flow cytometric analysis of somaclonal variation in lineages of *Hosta* sports detects polyploidy and aneuploidy chimeras, German Botanical Society and the Toyal Botanical Society of the Netherlands, Jun. 2, 2012, pp. 972-979,DOI: 10.1111/j.1438-8677.2012.00584.x.*

Title 35—Patent 103, Conditions for patentability; non-obvious subject matter, Historical and Revision Notes, p. 42.*

* cited by examiner

*Primary Examiner* — Anne Marie Grunberg
(74) *Attorney, Agent, or Firm* — Penny J. Aguirre

(57) ABSTRACT

A new cultivar of *Hosta* plant named 'VER10234' that is characterized by its young leaves that emerge white in color with green veins, maturing leaves that slowly develop streaks that are green in color, and fully mature leaves that turn all green in color (viridescent effect), its flowers that are lavender in color, and its flowers that are held horizontal to slightly dropping on the flowering stem.

3 Drawing Sheets

Botanical classification: *Hosta undulata.*
Cultivar designation: 'VER10234'.

BACKGROUND OF THE INVENTION

The present invention relates to a new and distinct cultivar of *Hosta undulata* and will be referred to hereafter by its cultivar name, 'VER10234'. 'VER10234' represents a new *Hosta* grown for use as a landscape plant.

The new cultivar arose as a mutation of *Hosta* 'White Feather' (not patented) in which tissue culture explants were treated with oryzalin by the Inventor Noordwijk, The Netherlands to double the chromosomes. 'VER10234' was selected in spring of 2016 from the plants that resulted from the treatment and evaluation from within the population of planta obtained. After oryzalin treatment; the plants were measured for the weight of the nuclei with a flowcytometer to indicate ploidy level. The tetraploid plants that were evaluated unexpectly varied greatly in leaf shape, fertility, and in particular the emergence and lastingness of the white coloration of the leaves. Some of the plants emerged green, other emerged white and quickly reverted to green typical of the parent plant, while 'VER10234' exhibited white coloration that was long lasting into the season. The stability through multiple rounds of dividing in tissue culture of the long lasting white coloration is thought to possibly be due to changes in plastid or chlorophyll development; an unexpected result.

Asexual propagation of the new cultivar was first accomplished by tissue culture using meristematic tissue under the direction of the Inventor in Heerhugowaard, The Netherlands in 2018. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'VER10234' as a new and unique cultivar of *Hosta.*

1. 'VER10234' exhibits young leaves that emerge white in color with green veins, maturing leaves that slowly develop streaks that are green in color, and fully mature leaves that turn all green in color (viridescent effect).
2. 'VER10234' exhibits flowers that are lavender in color.
3. 'VER10234' exhibits flowers that are held horizontal to slightly dropping on the flowering stem.

4. 'VER10234' exhibits flowers that are open trumpet in form.
5. 'VER10234' exhibits fertile flowers.

The parent plant of 'VER10234', 'White Feather', differs from 'VER10234' in having leaves and flowers that are thinner in substance, more numerous, and smaller in size, flowers that are nearly closed trumpet in form, held more downward on the flowering stems, and smaller in size, in producing more shoots that are smaller and thinner in substance, in having white foliage that very quickly becomes green (viridescent), and in being sterile. 'VER10234' can be most closely compared to *Hosta undulata* 'Albomarginata' (not patented). 'Albomarginata' differs from in lacking the robust "tetraploid" features in having smaller and thinner leaves, stems, and flowers, in having foliage with green centers and white margins as young and mature leaves that lack viridescent coloration (light colored foliage that turns green with maturity).

BRIEF DESCRIPTION OF THE DRAWINGS

The accompanying color photographs illustrate the overall appearance and distinct characteristics of the new *Hosta*. The photographs were taken of a 3 year-old plant as grown an unheated greenhouse in a 27-cm container in Noordwijk, The Netherlands.

Figure 1:
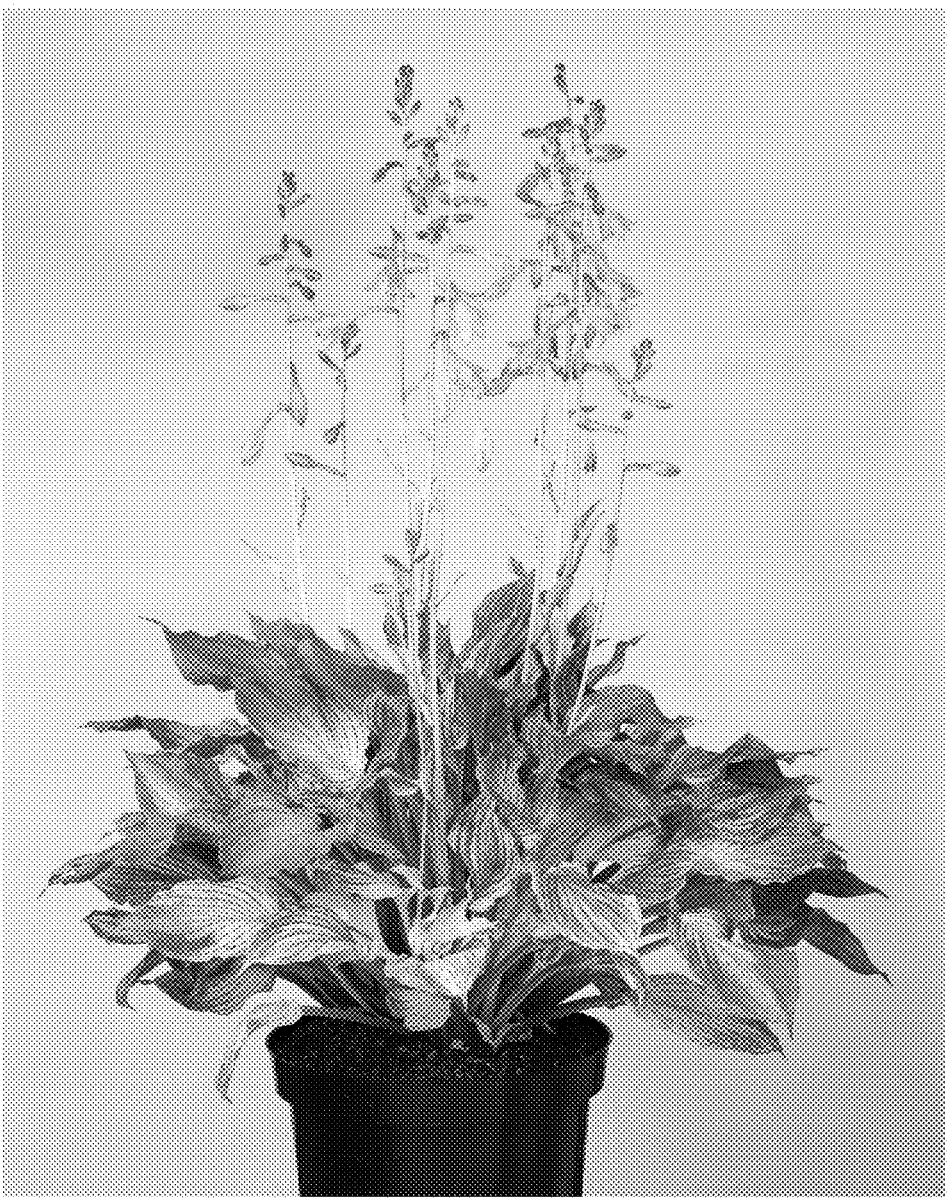
FIG. 1 provides an overall view of a plant of 'VER10234' in bloom.
Figure 2:
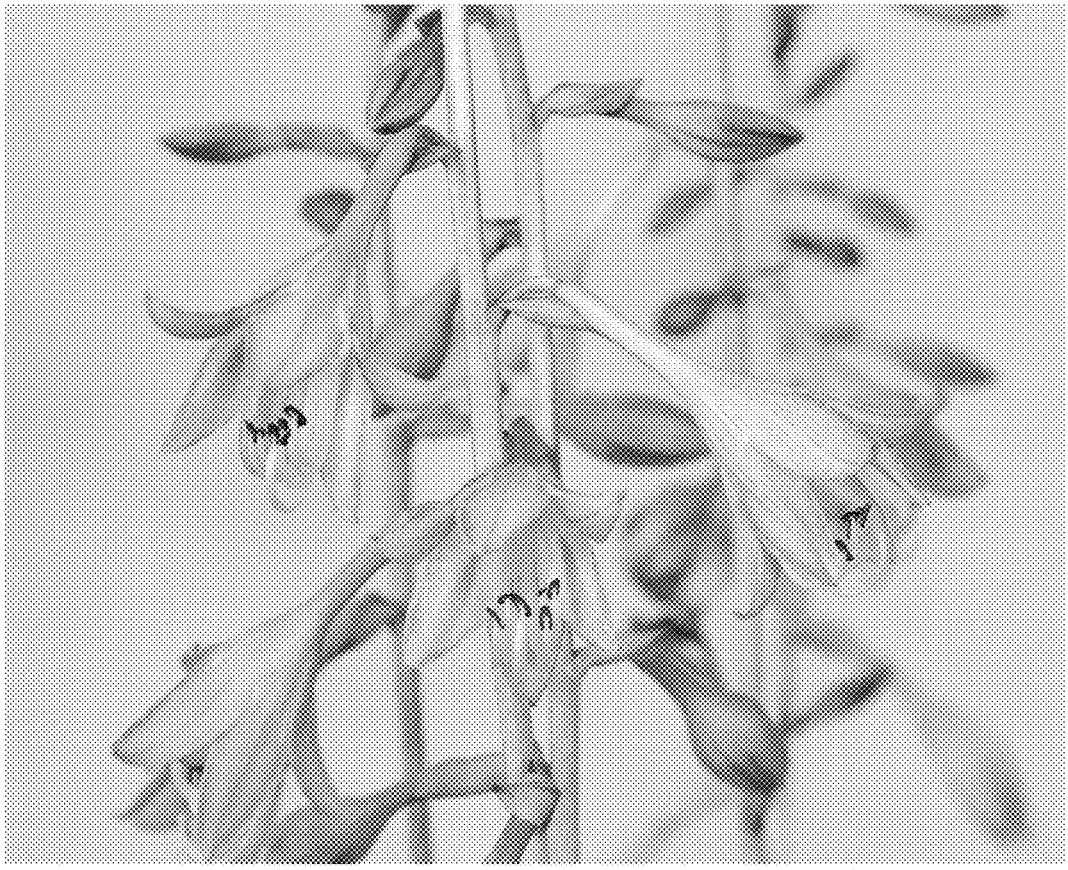

The photograph in FIG. 2 provides a close-up view of an inflorescence of 'VER10234'.

Figure 3:
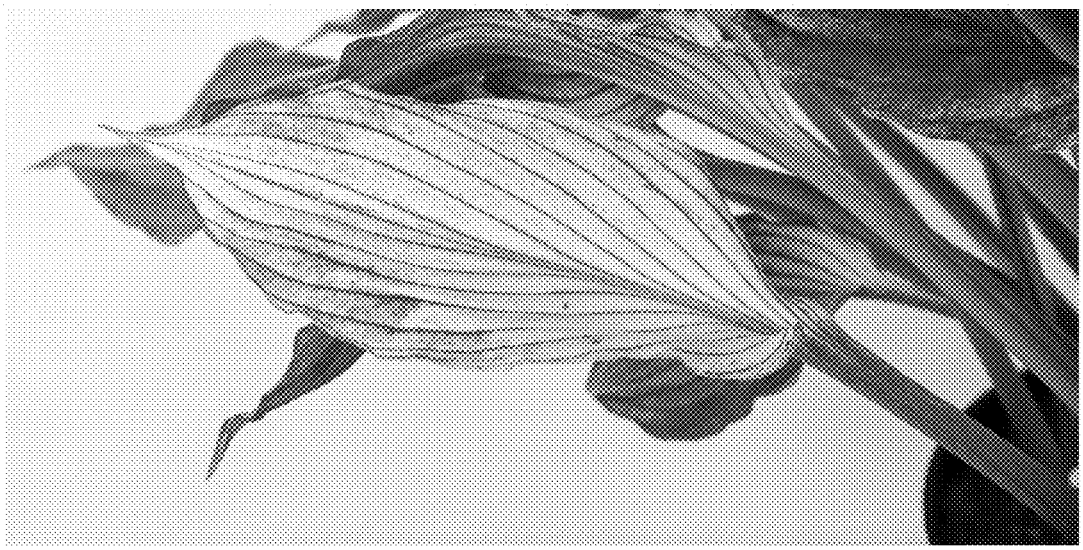

FIG. 3 provides a close-up view of the young leaves of 'VER10234'.

Figure 4:
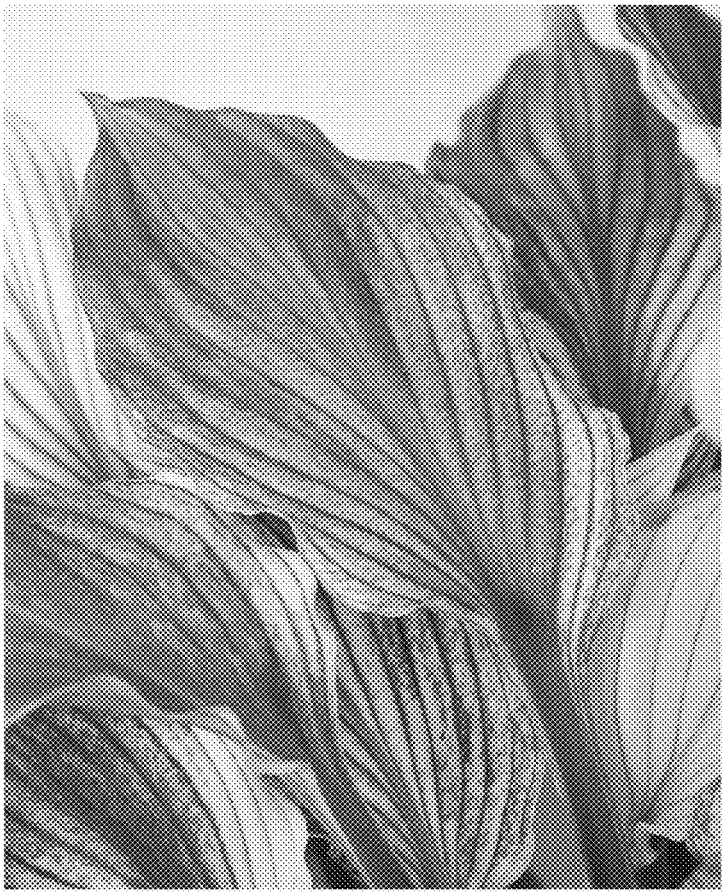

FIG. 4 provides a close-up view of the maturing leaves of 'VER10234'.

The colors in the photographs may differ slightly from the color values cited in the detailed botanical description, which accurately describe the colors of the new *Hosta*.

DETAILED BOTANICAL DESCRIPTION OF THE PLANT

The following is a detailed description of 3-year-old plants as grown in an unheated greenhouse in 27-cm containers in Noordwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—End of July into August in The Netherlands.

*Plant type*.—Herbaceous perennial.

*Plant habit*.—Flattened globular, broadly spreading and upright.

*Height and spread*.—An average of 42.1 cm in height (to top of foliage), 85 cm in height (to top of inflorescence), 77.5 cm in spread.

*Cold hardiness*.—At least in U.S.D.A. Zones 5.

*Diseases and pests*.—No susceptibility or resistance to diseases or pests has been observed.

*Root description*.—Freely branched, fleshy.

*Root development*.—About 6 weeks to produce a fully rooted plant in a 13-cm container from a tissue culture plug.

*Propagation*.—Tissue culture.

*Growth rate*.—Moderately vigorous.

Foliage description:

*Leaf shape*.—Broadly ovate.

*Leaf division*.—Simple.

*Leaf base*.—Broad attenuate.

*Leaf apex*.—Apiculate.

*Leaf venation*.—Camptodrome pattern, upper surface color; 143A, lower surface color; 146B.

*Leaf margins*.—Entire, coarsely undulate.

*Leaf attachment*.—Petiolate.

*Leaf arrangement*.—Alternate, in basal rosettes.

*Leaf surface*.—Upper and lower surface is glabrous, smooth, very slightly glossy and leathery, non-rugose, matte.

*Leaf orientation*.—Held nearly upright to slightly outward on upright petioles.

*Leaf color*.—Young upper surface; a blend of 10C and 160C, young leaf lower surface; a blend of 9D and 160C, mature upper surface; a blend of 150D and 157A, changing to a blend of 144A, 144B and 146A in summer, mature lower surface; a blend of 150D and 157A, changing to a blend of 137C and 143A in summer.

*Leaf size*.—Average of 17.3 cm in length and 10.2 cm in width.

*Leaf quantity*.—Average of 9 per basal rosette.

*Petioles*.—Strong, average of 24.7 cm in length, average of 1.3 cm in diameter, both surfaces are very slightly glossy, color; upper surface 143C and 144B, margined 144A, color lower surface 145D, changing to 145B towards the margins, margins 144A.

Flower description:

*Inflorescence type*.—Terminal racemes of single open trumpet-shaped flowers.

*Inflorescence size*.—28.2 cm in height, 13.3 cm in width.

*Lastingness of inflorescence*.—About 4 weeks from first opening bloom to fading of last opening bloom, individual blooms last up to 5 days, self cleaning.

*Flower type*.—Trumpet, single.

*Flower/inflorescence number*.—Average of 9 inflorescences per plant, 20 flowers per inflorescence, 200 buds and flowers per plant.

*Flower fragrance*.—None.

*Flower aspect*.—Held horizontal to slightly drooping.

*Flower buds*.—Average of 2.9 cm in length, 8 mm in diameter, oblanceolate in shape, smooth, glabrous and moderately glossy surface, color; 85A, blotched N82B to N82C.

*Flower size*.—Average of 7.2 cm in depth, 4.5 cm in length, 5 cm in diameter, flower throat diameter 1 cm, flower tube length 3.7 cm, flower tube 5 mm in diameter.

*Peduncles*.—An average of 79.8 cm in length, 5 mm in diameter, held in an average angle of 10°, strong, smooth and glabrous surface, color; 150D, tinged at the nodes 185B, top 186B and 186C.

*Pedicels*.—An average of 1.3 cm in length, 2.25 mm in diameter, held in an average angle of 70°, moderately strong, smooth and glabrous surface, 76C, tinged with 146C in color.

*Calyx*.—Campanulate in shape, 7.2 cm in length, 4.5 cm in diameter.

*Tepals*.—6, rotate, fused into campanulate shape, 50% of the tepals are fused, glabrous, slightly glossy and dull surfaces, entire margins, acute apex, 7.2 cm in length, outer tepal 1.45 cm in width, color; when opening and fully open upper surface outer tepals 76A, changing to 76B at the top, margins 76D, base N155B, inner tepals a blend of 76C and 76D, top 76B, central band 76A, base a blend of N155B and NN155B, fading to 85A and 86D, when opening and fully open lower surface 76B, main vein on inner tepal 77B, fading to 85A and 86D, veins on outer tepal 77B, other veins match leaf surface, throat; a blend of N155B and NN155B, tube 76B.

*Floral bracts*.—1 at the base of each pedicel, ovate in shape, apiculate apex, truncate base, both surfaces are smooth and glabrous, average of 2.7 cm in length and 1.4 cm in width, color of both surfaces 157C, base 144B, main vein on lower side 144B.

Reproductive organs:

*Gynoecium*.—Pistil; 1, 7.2 cm in length, style; 7.1 cm in length, 157D, stigma; crested in shape, 1 mm in length and diameter, 157D in color.

*Androecium*.—Stamens; 6, filament; 6.5 cm, 157D in color, anthers; elliptic in shape, 4 mm in length, 1.5 mm in width, N186B in color, pollen is abundant and 14A in color.

*Fruit/seed*.—Production of seed capsules has not been observed to date.

It is claimed:

1. A new and distinct cultivar of *Hosta* plant named 'VER10234' as herein illustrated and described.

* * * * *